United States Patent [19]

Zupancic et al.

[11] Patent Number: 4,984,774
[45] Date of Patent: Jan. 15, 1991

[54] PATIENT SUPPORT COUCH ASSEMBLY

[75] Inventors: Anton Z. Zupancic, Kirtland; Anthony A. Champa, Euclid; John L. Dobbs, Broadview Heights, all of Ohio

[73] Assignee: Picker International, Inc., Highland Hts., Ohio

[21] Appl. No.: 276,287

[22] Filed: Nov. 25, 1988

[51] Int. Cl.$^5$ ............................................. A61G 13/00
[52] U.S. Cl. ..................................... 269/322; 254/122
[58] Field of Search ............... 269/322, 328; 254/122, 254/124, 126

[56] References Cited

U.S. PATENT DOCUMENTS

| | | | |
|---|---|---|---|
| 4,131,802 | 12/1978 | Braden et al. | 250/445 T |
| 4,567,894 | 2/1986 | Bergman | 128/653 |
| 4,613,122 | 9/1986 | Manabe | 269/322 |
| 4,641,823 | 2/1987 | Bergman | 269/322 |
| 4,657,235 | 4/1987 | Schär | 269/322 |
| 4,674,107 | 6/1987 | Urban et al. | 378/98 |
| 4,715,591 | 12/1987 | Dragmen | 269/322 |
| 4,727,328 | 2/1988 | Carper et al. | 324/318 |
| 4,771,785 | 9/1988 | Duer | 128/653 |
| 4,773,637 | 9/1988 | Jarin | 269/322 |

Primary Examiner—J. J. Harman
Attorney, Agent, or Firm—Fay, Sharpe, Beall, Fagan, Minnich & McKee

[57] ABSTRACT

A medical diagnostic couch assembly for a patient undergoing medical diagnosis includes a base, a couch on which the patient reclines and a mounting frame for slidably supporting the couch. The mounting frame includes a longitudinally extending slot and a pair of parallel vertically spaced hard metal wear strips, one secured to a respective top and bottom surface of the slot. The couch includes at least one rail cover for enclosing the slot to retard the deposition of dirt and grime therein. The couch further includes at least one roller rotatably mounted to the rail cover wall so as to extend into the slot and between the pair of wear strips. A scissors structure supports the mounting frame. The scissors structure includes a first leg and a second leg with each of the legs being rotatably secured at a first end to the base and at a second end to the mounting frame. The two legs are also secured together at an intermediate portion of each leg. A motor is provided for selectively powering the scissors structure to pivot the structure and thereby move the couch and the mounting frame.

19 Claims, 7 Drawing Sheets

PATIENT SUPPORT COUCH ASSEMBLY

BACKGROUND OF THE INVENTION

The present invention relates generally to patient support structures. More particularly, the present invention deals with a patient support couch or table assembly adapted to be used with a diagnostic imaging apparatus.

More specifically, the present invention relates to a patient positioning couch associated with a CT scanner. However, it should be appreciated by those skilled in the art that the couch can also be utilized with various other types of medical diagnostic apparatuses such as magnetic resonance imaging apparatus or X-ray apparatus.

Computerized tomography (CT) apparatus is well known. The CT scanner is quite popular as a tool for diagnosis of tumors and the like. Owing to good quality tomographic images with low dosage X-ray radiation, the CT scanner has become well accepted by the medical profession. CT scanners have a circular opening in which an X-ray beam and an opposing scintillator-type detector are translated and rotated according to well known procedures.

In order to obtain tomographic images of a patient with a CT scanner or X-ray CT apparatus, it is necessary that the patient be located exactly at a predetermined position inside the opening of a scan gantry of the apparatus. For this reason, such apparatus has been provided with a patient handling couch which is moveable vertically to be in line with the scan gantry, and horizontally in and out of the scan gantry. Several couches are known for this purpose. However, various difficulties have been experienced with the known couches. Among these are the fact that dirt, dust and liquids can accumulate in the rail mechanism on which the couch moves in and out of the scan gantry. Another problem is that there is a considerable amount of rolling resistance experienced by the conventional rollers which allow movement of the couch in and out of the scan gantry. Sometimes the couch also experiences binding.

For those couches which do provide a scissors type mechanism for the elevation of the couch and its subframe from a base, the conventional scissors assemblies are not stable, rigid and able to accurately elevate the couch and its subframe to a desired height. The known conventional scissors mechanisms, while they are advantageous in the abstract, suffer in practice also from torque as well as deflection problems and are not provided with as stable and as solid a support base as would be desirable.

Accordingly, it has been considered desirable to develop a new and improved patient support couch or table apparatus which would overcome the above-referenced problems and others and provide a new and improved table construction.

BRIEF SUMMARY OF THE INVENTION

In accordance with the present invention, there is provided a medical diagnostic couch assembly for a patient undergoing medical diagnosis.

More particularly in accordance with this aspect of the invention, the couch assembly comprises a base, a couch on which the patient reclines and a subframe for slidably supporting the couch. The subframe includes a longitudinally extending slot and a pair of parallel vertically spaced hard metal wear strips one secured to a respective top and bottom surface of the slot. The couch includes at least one rail cover wall for enclosing the slot to retard the deposition of dirt and grime therein. The couch further includes at least one roller rotatably mounted to the rail cover wall so as to extend into the slot and between the pair of wear strips. A scissors structure is provided for supporting the mounting subframe and the couch. The scissors structure comprises a first leg and a second leg each of the legs being rotatably secured at a first end to the base and at a second end to the mounting frame. The two legs are also secured to each other. A means is provided for selectively pivoting the scissors structure.

According to another aspect of the invention, an examination table or couch is provided.

More particularly in accordance with this aspect of the invention, the table comprises a base member fixedly secured to a floor surface, a couch on which a patient can recline and a subframe on which the couch is slidably mounted. A scissors structure is provided for supporting the subframe and selectively elevating the subframe, and hence the couch, from a lower position to an upper position. A driving means is provided for selectively driving the couch in a forward and a reverse direction in relation to the subframe. The driving means includes a motor and a clutch. A bypass system is provided for selectively bypassing the driving means and manually moving the couch. The system comprises a handle and a line switch which is actuated when the handle is grasped to disconnect the clutch and allow manual movement of the couch in relation to the subframe.

One advantage of the present invention is the provision of a new and improved medical diagnostic table or couch.

Another advantage of the present invention is the provision of a medical diagnostic table which is provided with a single scissor jack which resists torque and deflection and provides stability, rigidity and accuracy in its movement from a lower position to an upper position.

Still another advantage of the present invention is the provision of a patient support table which does not have any opening slots or grooves on either the couch or tabletop portion or on the supporting subframe thereby protecting the drive mechanism of the couch portion from contamination by dirt, fluids and the like.

Yet another advantage of the present invention is the provision of a patient support table in which the horizontal movement of the couch in relation to its subframe is done by wheels moving on a pair of hard rolling surfaces in order to decrease rolling resistance and to distribute the concentrated stresses under the wheels.

A further advantage of the present invention is the provision of a patient support table in which a horizontal driving means for the couch portion in relation to its subframe is so confined that both the guiding and the driving are provided on the same side of the couch to prevent binding.

A still further advantage of the present invention is the provision of a patient support table in which a means is provided for disconnecting a power drive for a tabletop so that the tabletop can then be freely moved manually to position a patient in a diagnostic scanner or to extract the patient from the scanner.

A yet further advantage of the present invention is the provision of a patient support couch having a couch portion which can be moved either by a motor or manually and in which an indexing system for indicating the position of the couch continues to function even when the motor is disconnected.

Still other advantages of the present invention will become apparent to those skilled in the art upon a reading and understanding of the following detailed description.

BRIEF DESCRIPTION OF THE DRAWINGS

The invention may take physical form in certain parts and arrangements of parts a preferred embodiment of which will be described in detail in this specification and illustrated in the accompanying drawings which form a part hereof and wherein.

DETAILED DESCRIPTION OF THE PREFERRED EMBODIMENT

Figure 1:
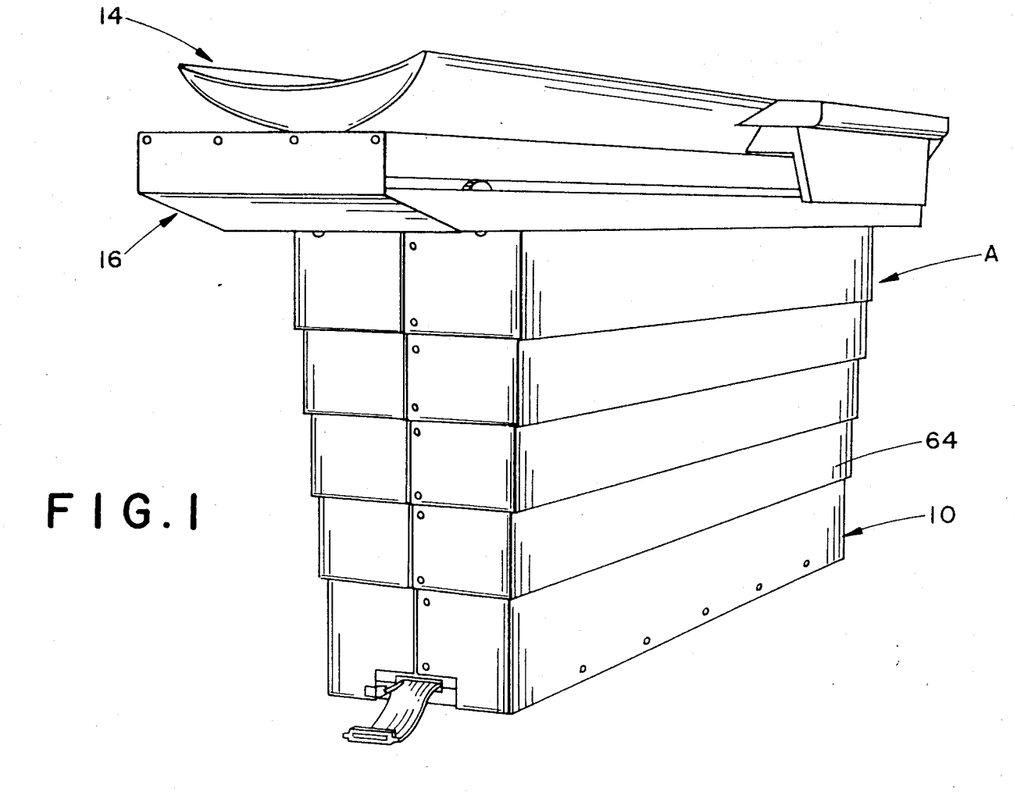
FIG. 1 is a perspective view of the patient support couch assembly according to the present invention.

Referring now to the drawings, wherein the showings are for purposes of illustrating the preferred embodiment of the invention only and not for purposes of limiting same, FIG. 1 shows a patient support couch A which is adapted to be used with a medical diagnostic imaging system. The imaging system can be a computerized tomography (CT) scanner system. However, it should be recognized that the patient support couch A could also be used for various other types of imaging environments as well as for patient support for other purposes.

Figure 2:
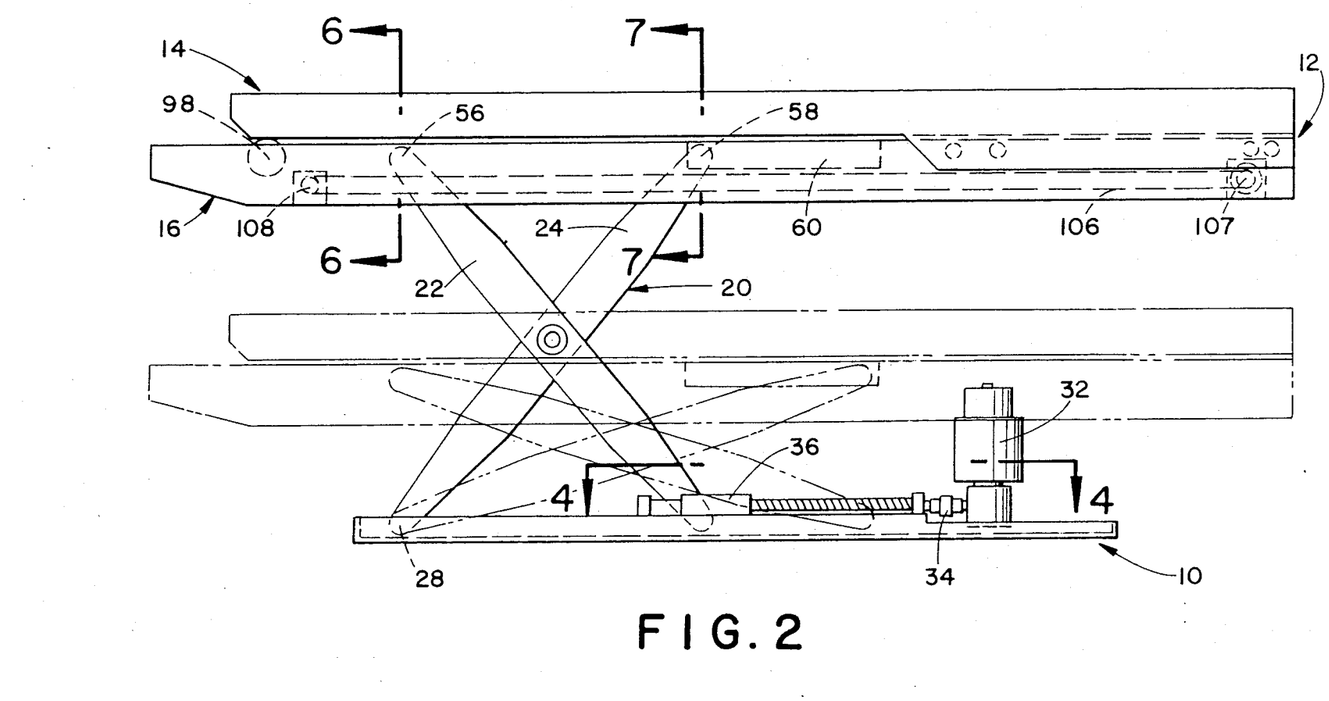
FIG. 2 is a side elevational view of the couch assembly of FIG. 1.

More particularly, and with reference to FIG. 2, the patient support couch includes a base 10 and a top portion 12 which comprises a couch section 14 and a subframe section 16 upon which the couch is slidably supported. A scissors assembly 20 is provided between the base and the top.

Figure 3:
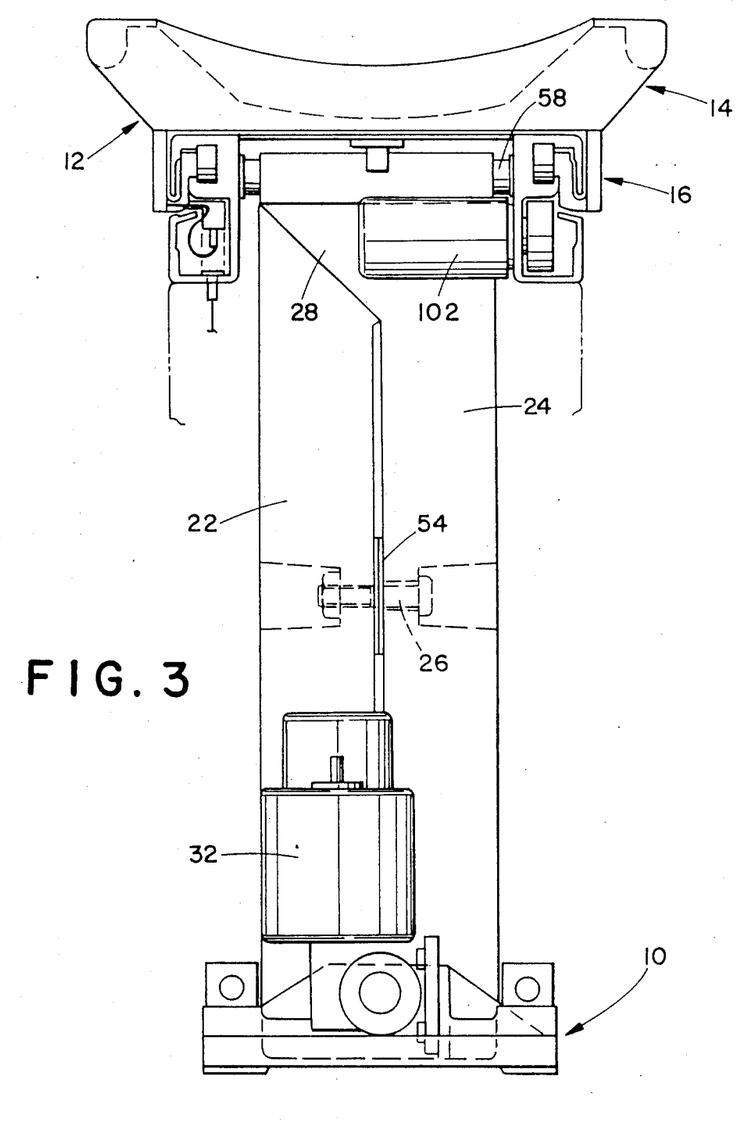
FIG. 3 is an enlarged end elevational view of the couch assembly of FIG. 2.
Figure 4:
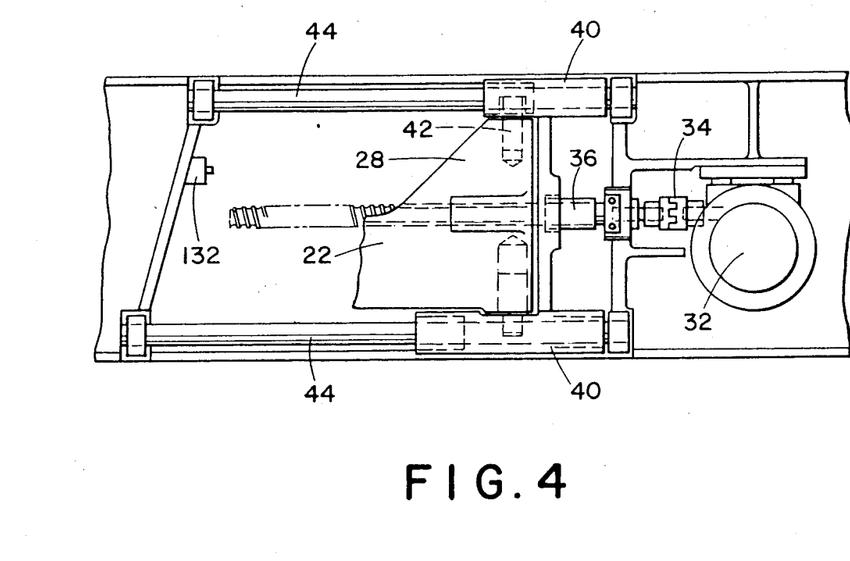
FIG. 4 is an enlarged cross-sectional view along line 4—4 of the couch of FIG. 2.

With reference now also to FIG. 3, the scissors assembly 20 comprises a first scissor leg 22 and a second scissor leg 24 which are connected at their midpoints by a pivot pin 26. In other words, each leg has a width of somewhat less than one-half the width of the base 10. However, both legs include flange sections 28 at their top and bottom edges so that the legs extend the full width of the base 10 adjacent the base and the full width of the top 12 adjacent the top. In this way, the second leg 24 can be rigidly secured at a pivot 28 by fasteners (not illustrated) to both sides of the base. With reference now also to FIG. 4, adjacent a lower end of the first leg 22 is a vertical drive motor 32 which is connected by a shaft coupling 34 to a ball screw assembly 36. The ball screw assembly is, in turn, secured to a lower end of the first scissor leg 22. As mentioned, the first scissor leg is provided with a flange section 28 so that the leg can be secured to each of a pair of slide bushings 40 by suitable fasteners 42. The slide bushings are, in turn, slidably mounted on a pair of scissor shafts 44 which extend along the two side edges of the base section 10.

In this way, upon actuation of the vertical drive motor, the first scissor leg 22 can be slidably moved from a lower, rest position to a position approaching the second scissor leg base. In this way the top 12 of the support couch can be elevated. In order to make sure that the scissor legs do not have any play between them, a zero clearance adjustment screw (not illustrated) can be provided at the base of the second leg 24. This adjustment means insures that the only distance between the first and second legs is that required by a bearing washer 54 which is provided between the legs adjacent their pivot point as defined by the pivot pin 26.

With reference again to FIG. 2, the first leg 22 is rigidly secured at a pivot 56 to the subframe 16. In contrast, the second leg 24 is secured at a moveable pivot 58 in a subframe guide 60 that is fastened to the subframe 16. In this way a scissoring motion can take place between the base 10 and the top 12 as the top is elevated or lowered in relation to the base by actuation of the vertical drive motor 32.

The scissor legs 22, 24 are preferably tubular and made of a suitable material, such as metal, to resist torque as well as deflection. The zero clearance adjustment enhances the stability, rigidity and accuracy of the scissor structure. The base 10 is designed to provide a stable and solid support to the scissor jack 20. The base is rigidly mounted on a suitable floor surface, such as by conventional bolts or the like (not illustrated).

In order to protect the scissors assembly 20 from contamination, a collapsible skirt 64 extends from the subframe 16 down to the ground as can be seen from FIG. 1. The skirt can be suitably secured to both the subframe 16 and the base 10. As the scissors assembly moves up and down, the skirt 64 can accommodate the scissoring motion of the couch A while protecting the scissors structure from contamination.

Figure 6:
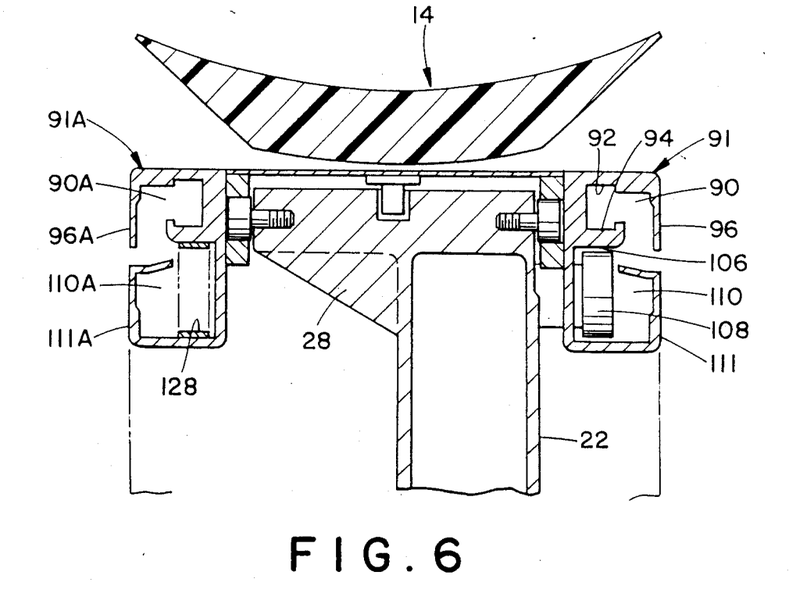
FIG. 6 is a cross-sectional view along line 6—6 of the couch of FIG. 2.
Figure 7:
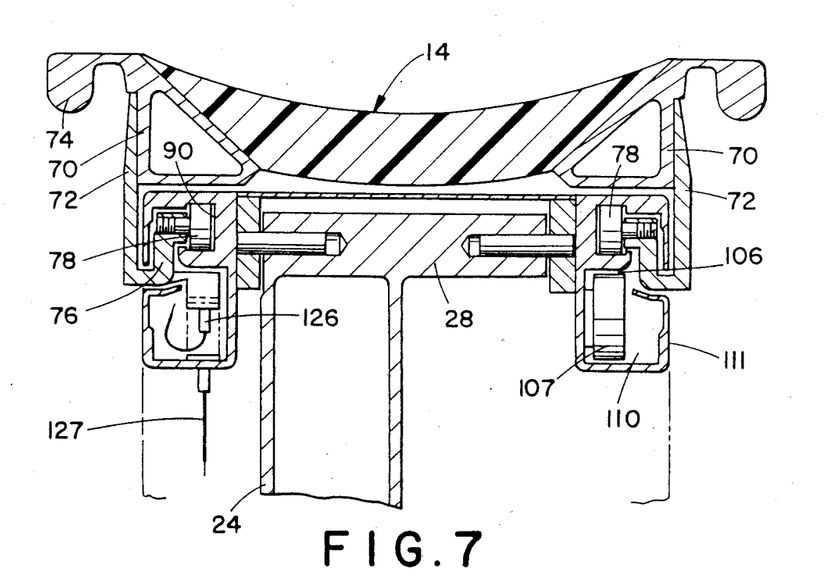
FIG. 7 is a cross-sectional view along line 7—7 of the couch of FIG. 2.

With reference now to FIG. 7, the couch 14, which can be made of a suitable conventional material, is fastened to a pair of triangular side frame members 70 to provide support therefor. Fastened to each side frame 70 is a couch side wall or cover wall 72. Couch handles 74 can be provided which are integral with the frame members 70, if desired. An inwardly extending bracket section 76 of the cover 72 rotatably supports at least one roller or wheel 78. Such wheels 78 are provided on both sides of the couch as is evident from FIGS. 6 and 7.

The wheel 78 extends into a slot 90 which is formed in a side wall 91 of the subframe 16. Since the subframe wall 91 is preferably made of a light relatively malleable material such as aluminum, the slot is provided with upper and lower hardened metal wear strips, 92, 94 which can preferably be made from a steel material or the like, as can be better seen from FIG. 6. The wear strips provide a hard rolling surface to decrease rolling resistance as the couch is moved in relation to the subframe 16 and to distribute the concentrated stresses under the wheel 78 over a larger area of the subframe.

The subframe side wall 91 outwardly of the slot 90 is provided with a flange 96 which extends downwardly to cover the slot, to prevent anything from falling into the slot such as dirt or the like and to prevent liquid from splashing into the slot. It can be seen from FIG. 6 that the slot 90 is suitably protected against the entry of foreign material thereon which would be deleterious to the correct sliding operation of the couch in relation to the subframe.

To assist the sliding operation of the couch 14 in relation to the subframe 16, a roller 98 is provided adjacent a front end of the table as is best seen in FIG. 2. The roller 98 is preferably centrally positioned between the sides of the subframe 16.

Figure 5:
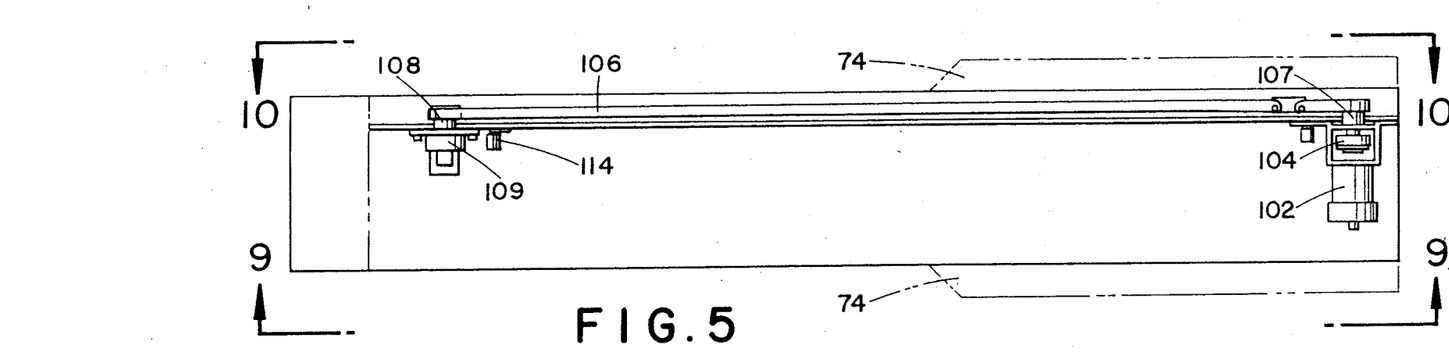
FIG. 5 is a top plan view of the couch of FIG. 2.

For actuating the motion of the couch in relation to the subframe, a horizontal drive motor 102 is provided, as is shown in FIG. 5. Connected to the motor is a clutch mechanism 104 that selectively allows the motor to act upon an inextensible metal band 106 through a drive wheel or pulley 107. To correctly tension the metal band 106, a front pulley or wheel 108 is provided. This wheel is pivotably mounted to the subframe sidewall by a housing 109. As shown in FIG. 6, The band is located in a second slot 110 which is defined in the subframe side wall 91. The band is operatively connected also to the side frame wall 72 which is fastened to the couch portion 14. To protect the band 106 in the second slot 110, the slot is enclosed by a further flange member 111 of the subframe side wall 91. This may be more clearly evident from FIGS. 5 and 6. The band 106 is operably connected to the couch 14 so that movement of the band moves the couch.

The metal band or tape 106 for driving the couch 14 in relation to the subframe 16 is only provided on one side of the table assembly, namely the right side as viewed in FIGS. 5, 6 and 7. Also provided on the right side of the table is a position coder means 114 as best seen in FIG. 5 to indicate the location of the couch 14 in relation to the subframe 16. The coder is a digital device which includes a pulley or wheel (not visible) that is rotated by a movement of the metal band 106.

Figure 8:
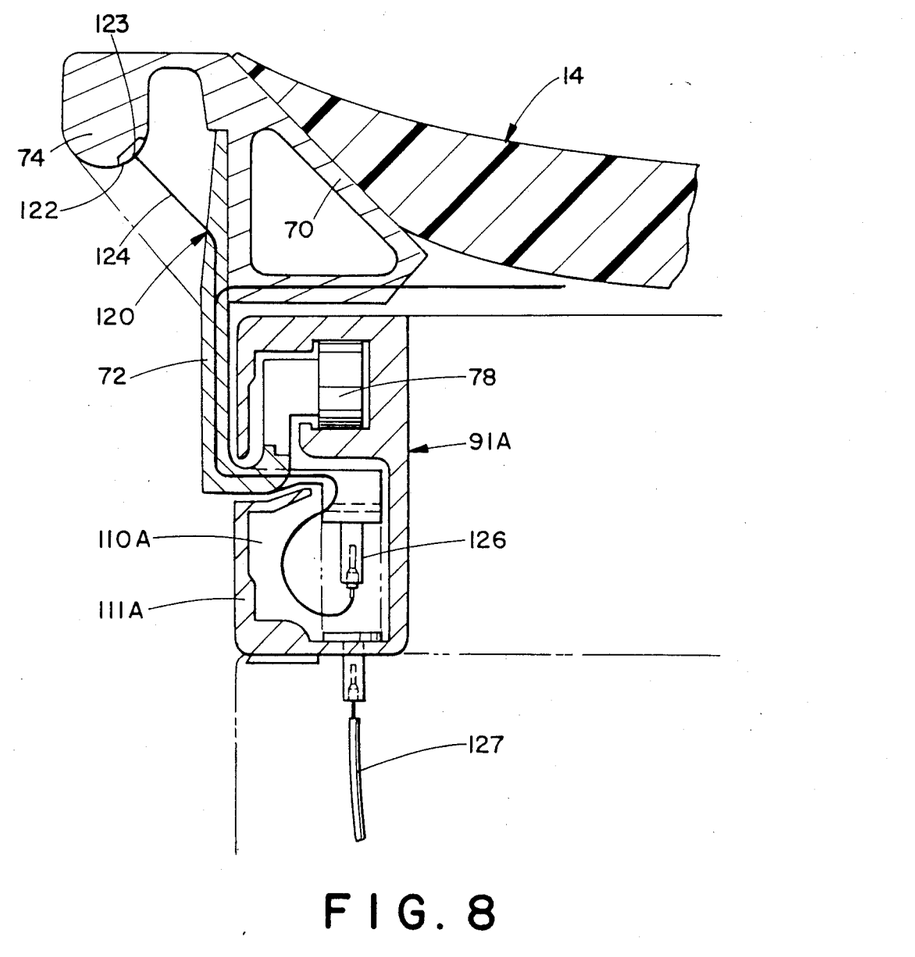
FIG. 8 is an enlarged cross-sectional view of a portion of the couch of FIG. 7.
Figure 9:
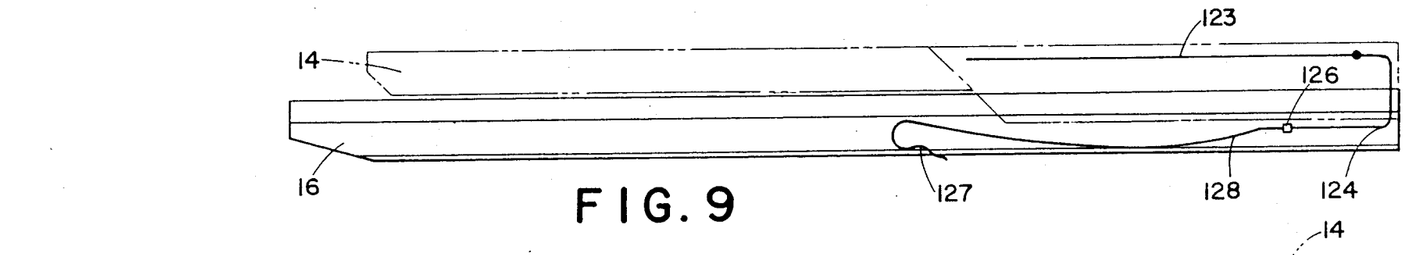
FIG. 9 is a side elevational view along line 9—9 of the couch of FIG. 5.
Figure 10:
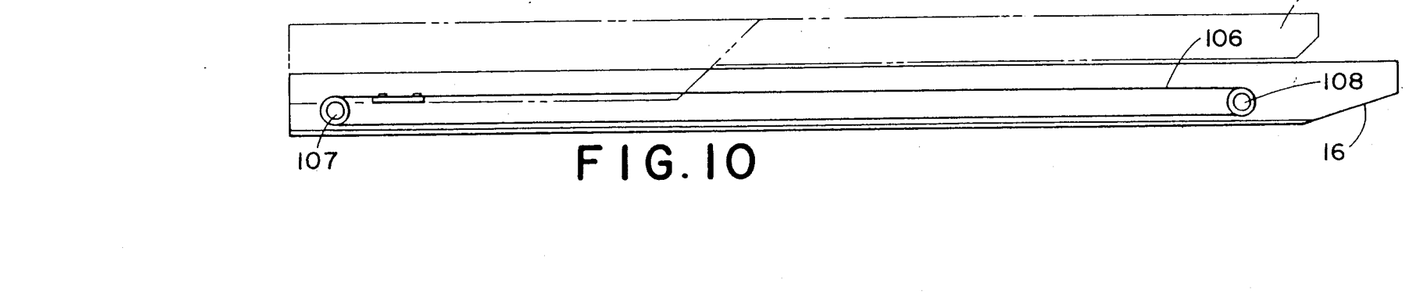
FIG. 10 is a side elevational view along line 10—10 of the couch of FIG. 5; and, FIG. 11 is a top plan view of a section of the couch of FIG. 5.

With reference now to FIG. 8, the handle 74, which also serves as the side rail for the couch, includes a means 120 for selectively disconnecting the horizontal drive motor 102 from the metal band 106. The disconnecting means comprises a grip portion 122 which extends for a considerable length on the handle 74, such as approximately 3 feet. Extending longitudinally along most of the length of the grip portion is a tape switch 123 as best shown in FIG. 9. A cable 124 leads from the tape switch to a flat cable support 126 that is illustrated in FIG. 8. This cabling can be provided in a slot 110A in the left hand side frame wall 72 as is evident from FIGS. 6 and 7. A flange 111A encloses the slot 110A to protect it. Gripping the switch 123 anywhere along its length will break the circuit to the motor clutch 104 thus disconnecting the motor 102 from the pulley 107. Maintaining the pressure on the tape switch 123 will enable the couch 14 to be manually moved in relation to the subframe 16 as desired.

However, although the motor 102 no longer acts on the metal band 106, the position coder means 114 remains operative so that the position of the patient can always be sensed even when the normal drive means for the couch is disconnected. One advantage of this arrangement of the position coder means 114 is that when the drive motor 102 is disconnected, the encoder can still provide positioning information. In this way, the table does not have to be realigned or reindexed each time the drive motor 102 is disconnected from the pulley 107, and hence the band, 106, by the clutch 104. Another advantage of the disconnect switch is that in the event of a power failure or medical emergency, the patient couch 16 can be readily removed from the diagnostic imaging structure simply by grasping the handle 74.

Figure 11:
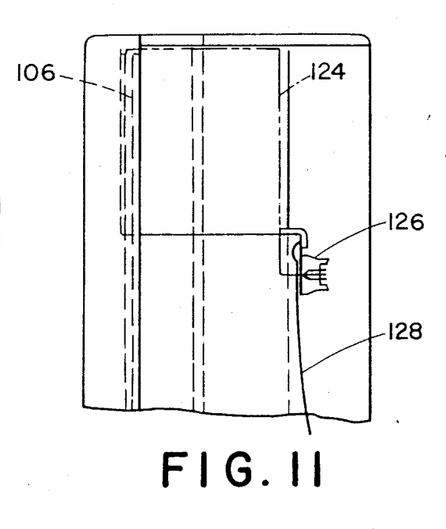

It should be appreciated that side rails 74 are provided on both sides of the couch assembly A as can best be seen from FIG. 5. A suitable hand operated switch means is provided in each of the side rails so that gripping either side rail will enable one to disengage the motor 102 from the metal band 106 for manual movement of the couch in relation to the subframe. For this purpose, and with reference now to FIGS. 9 and 11, a switch 127 is provided on the second handle 74 and a suitable cable 128 leads from the tape switch 127 to the flat cable support 126.

The scissor assembly for the vertical drive of the top 12 in relation to the base 10 as well as the horizontal drive assembly for moving the couch 14 in relation to the subframe 16 have been constructed in such a manner that they are very quiet and precise in their operation. In addition, the movements of the assembly A are quiet and smooth, without any jerkiness. In order to ensure that the scissors do not extend past a desired point, at least one limit switch 132 can be provided for the scissors drive assembly, as is best seen in FIG. 4. When the scissor structure contacts the limit switch 132, the vertical drive motor 32 will be disengaged and any further movement of the scissor structure in a vertical direction will be prevented.

The invention has been described with reference to a preferred embodiment. Obviously, modifications and alterations will occur to others upon a reading and understanding of this specification. It is intended to include all such modifications and alterations insofar as they come within the scope of the appended claims or the equivalents thereof.

Having thus described the invention, it is now claimed as:

1. A medical diagnostic couch assembly for a patient undergoing medical diagnosis, comprising:
    a couch on which the patient reclines said couch including a depending rail cover wall;
    a subframe for slidably supporting said couch, said subframe including longitudinally extending slot, and a pair of parallel vertically spaced hard metal wear strips, one secured to a respective top and bottom surface of the slot wherein said rail cover wall encloses said slot to retard the deposition of dirt and grime therein, said couch further including at least one roller rotatably mounted to said rail cover wall and extending inwardly therefrom so as to extend into said slot and between said pair of wear strips;
    a scissors structure for supporting said subframe, said scissors structure comprising a first leg and a second leg, each of said legs being pivotably secured at a first end to said base and at a second end to said subframe, said two legs also being secured to each other intermediate said first and second ends thereof; and,
    a means for selectively pivoting said scissors structure.

2. The assembly of claim 1 wherein two pairs of parallel vertically spaced wear strips are provided, one on either side of said subframe and two rail cover walls are provided and wherein at least one roller is rotatably mounted to each said rail cover wall, said roller rotating around a horizontally oriented axis, wherein one of said rollers extends between each of said pairs of spaced wear strips.

3. The assembly of claim 1 wherein said subframe slot is provided in a side wall housing of said subframe, said housing including two vertically spaced longitudinally extending slots and two vertically spaced flanges, each of which is adapted to substantially cover its respective slot.

4. The assembly of claim 1 wherein said couch further comprises a pair of rail cover walls and a pair of handles, one secured to each rail cover wall.

5. The assembly of claim 1, further comprising a motorized drive mechanism for moving said couch in relation to said subframe.

6. The assembly of claim 5 further comprising a means for deactivating said motorized drive mechanism and for manually moving said crouch in relation to said base, wherein said means comprises a manually actuable switch means for deactivating said motorized drive mechanism.

7. The assembly of claim 5 wherein said drive mechanism comprises:
an inelastic belt operatively connected to said couch and at least one wheel on which said belt is rotatably mounted to said subframe;
a drive motor; and
a clutch mechanism which selectively allows said motor to act on said inelastic belt.

8. The assembly of claim 1 wherein said first and second legs each comprise a tubular cast metal channel which has a width somewhat less than one half of a width of said base.

9. The assembly of claim 1 wherein said couch comprises:
a pair of spaced side support channels; and,
a bed positioned between said support channels and secured thereto.

10. An examination table or couch, comprising:
a base member fixedly secured to a floor surface;
a couch on which a patient can recline;
a subframe on which said couch is slidably mounted;
a means for supporting said subframe and selectively elevating said subframe, and hence said couch, from a lower position to an upper position;
a driving means for selectively driving said couch in a forward and a reverse direction in relation to said subframe, said driving means including a motor and a clutch; and,
a bypass system for selectively bypassing said driving means and manually moving said couch, said system comprising a handle and a switch operatively connected to said handle and to said clutch, said switch being actuated when said handle is grasped for disconnecting said clutch from said motor thereby allowing manual movement of said couch in relation to said subframe.

11. The examination table of claim 10 wherein said means for supporting comprises a scissors structure that comprises:
a first tubular leg which is pivotably secured at a first end to said base and at a second end to said subframe;
a second tubular leg which is pivotably secured at a first end to said base and at a second end to said subframe, said first and second legs being located in a side-by-side relationship and so sized that each leg has a width somewhat less than one half of a width of said base; and,
a pivot pin for securing said two legs together at an intermediate point of each leg between said first and second ends thereof.

12. The examination table of claim 11 further comprising a means for pivoting said scissors structure and thereby selectively elevating said subframe wherein said means for pivoting said scissors comprises:
a motor including a shaft;
a ball screw assembly operably connected to said motor shaft so that said rotation of said shaft will cause a rotation of said ball screw assembly;
a pair of scissors shafts, one being located on either side of said base;
a pair of slide bushings one being adapted to slide on each of said scissors shafts; and,
wherein said first leg first end is secured to said ball screw assembly and said slide bushings.

13. The examination table of claim 10 further comprising an adjusting means for adjusting a clearance between said first and second legs adjacent said pivot pin.

14. The examination table of claim 9 wherein said means for actuating further comprises a non-extensible band which is operatively connected to said couch and is adapted to be moved by said motor thereby longitudinally moving said couch in relation to said subframe.

15. The examination table of claim 14 wherein said non-extensible band rotates on a pair of pulleys, one of which is powered by said motor wherein said pulleys each rotate about horizontal axes.

16. The examination table of claim 12 further comprising an encoder means secured between said couch and said subframe for providing a reading as to the movement of said couch in relation to said subframe, and wherein a disconnection of said driving means does not disconnect said encoder means.

17. An examination table or couch comprising:
a couch top on which a patient can recline, said couch top including at least one depending side wall; and,
a supporting means for said couch top, said supporting means comprising:
a frame member,
a mounting means for slidably mounting said couch top horizontally along a longitudinal axis relative to said frame member, said mounting means including:
a guideway located between said frame member and said couch top,
at least one hard metal wear surface located on one surface of said guideway, and
at least one roller extending into said guideway and into contact with said at least one hard metal wear surface, and wherein said at least one roller is mounted to said couch top at least one depending side wall so that said roller rotates around a generally horizontally oriented axis.

18. The examination table of claim 17 further comprising a driving mechanism for selectively driving said couch top horizontally in relation to said frame member.

19. The examination table of claim 18 further comprising a bypass system for disengaging said driving mechanism and enabling a manual movement of said couch top in relation to said frame member when desired.

* * * * *